US006447751B1

(12) United States Patent
Weinstein et al.

(10) Patent No.: US 6,447,751 B1
(45) **Date of Patent: *Sep. 10, 2002**

(54) METHOD AND DEVICE FOR FACILITATING COMBINED AEROSOL AND ORAL TREATMENTS FOR DIABETES MELLITUS

(76) Inventors: Robert E. Weinstein, 177 Commonwealth Ave., Boston, MA (US) 02116; Allan M. Weinstein, 9205 Pegasus Ct., Potomac, MD (US) 20854

( * ) Notice: Subject to any disclaimer, the term of this patent is extended or adjusted under 35 U.S.C. 154(b) by 0 days.

This patent is subject to a terminal disclaimer.

(21) Appl. No.: 09/837,723

(22) Filed: Apr. 18, 2001

(51) Int. Cl.[7] ............................ A61K 9/12; A61K 9/00

(52) U.S. Cl. .......................... 424/45; 424/46; 424/464; 424/400
(58) Field of Search ........................... 424/45, 464, 46, 424/400

(56) References Cited

U.S. PATENT DOCUMENTS 6,187,291 B1 * 2/2001 Weinstein et al. ............ 424/45

OTHER PUBLICATIONS

Massi–Benedetti, M. et al., Cardiovascular risk factors in Type 2 diabetes: the role of hyperglycemia, Exp Clin Endocrinol Diabetes 1999;106 (Suppl. 4)S120–3.

Polonsky, K. S., Evolution of beta–cell dysfunction in impaired glucose tolerance and diabetes, Exp Clin Endocrinol Diabetes 1999;106 (Suppl. 4)S124–7.

Landgraf, R., Approaches to the management of postprandial hyperglycaemia, Exp Clin Endocrinol Diabetes 1999;106 (Suppl. 4)S128–32.

Moses, R., Repaglinide in combination therapy with metformin in Type 2 diabetes, Exp Clin Endocrinol Diabetes 1999;106 (Suppl. 4)S136–9.

Schatz, H., Preclinical and clinical studies on safety and tolerability of repaglinide, Exp Clin Endocrinol Diabetes 1999;106 (Suppl. 4)S144–8.

Skyler, Jay S. et al., Efficacy of inhaled human insulin in Type 1 diabetes mellitus;a randomized proof–of–concept study, Lancet 201;357:331–335.

Gale, Edwin A. M., Two cheers for inhaled insulin, Lancet 201;357:324–325.

Cefalu, William T. et al., Inhaled human insulin treatment in patients with Type 2 diabetes mellitus, Annals of Internal Medicine 2001;134:203–207.

Landgraf, Rudiger, Meglitinide analogues in the treatment of Type 2 diabetes mellitus, Drugs and Aging 2000;17(5):411–425.

Moses, Robert G. et al., Flexible meal–related dosing with repaglinide facilitates glycemic control in therapy–naïve Type 2 diabetes, Diabetes Care 2001;24:11–15.

Kalbag, Jyoti B. et al., Mealtime glucose regulation with nateglinide in health volunteers, Diabetes Care 2001;24:73–77.

Lefebvre, Pierre J. et al., Glucose metabolism and the postprandial state, European Journal of Clinical Investigation 1999;29 (Suppl. 2), 1–6.

(List continued on next page.)

*Primary Examiner*—Jose ' G. Dees
*Assistant Examiner*—M. Haghighatian
(74) *Attorney, Agent, or Firm*—Robert R. Deleault, Esq.; Mesmer & Deleault, PLLC

(57) ABSTRACT

A dispensing container which incorporates an aerosolizable topical insulin preparation, at least one oral hypoglycemic agent, and indicia and instructions for their coordinated use as a single therapeutic regimen for the treatment of diabetes mellitus in a human, and a method for treating diabetes mellitus which employs such a device.

18 Claims, 2 Drawing Sheets

OTHER PUBLICATIONS

Figure 1:
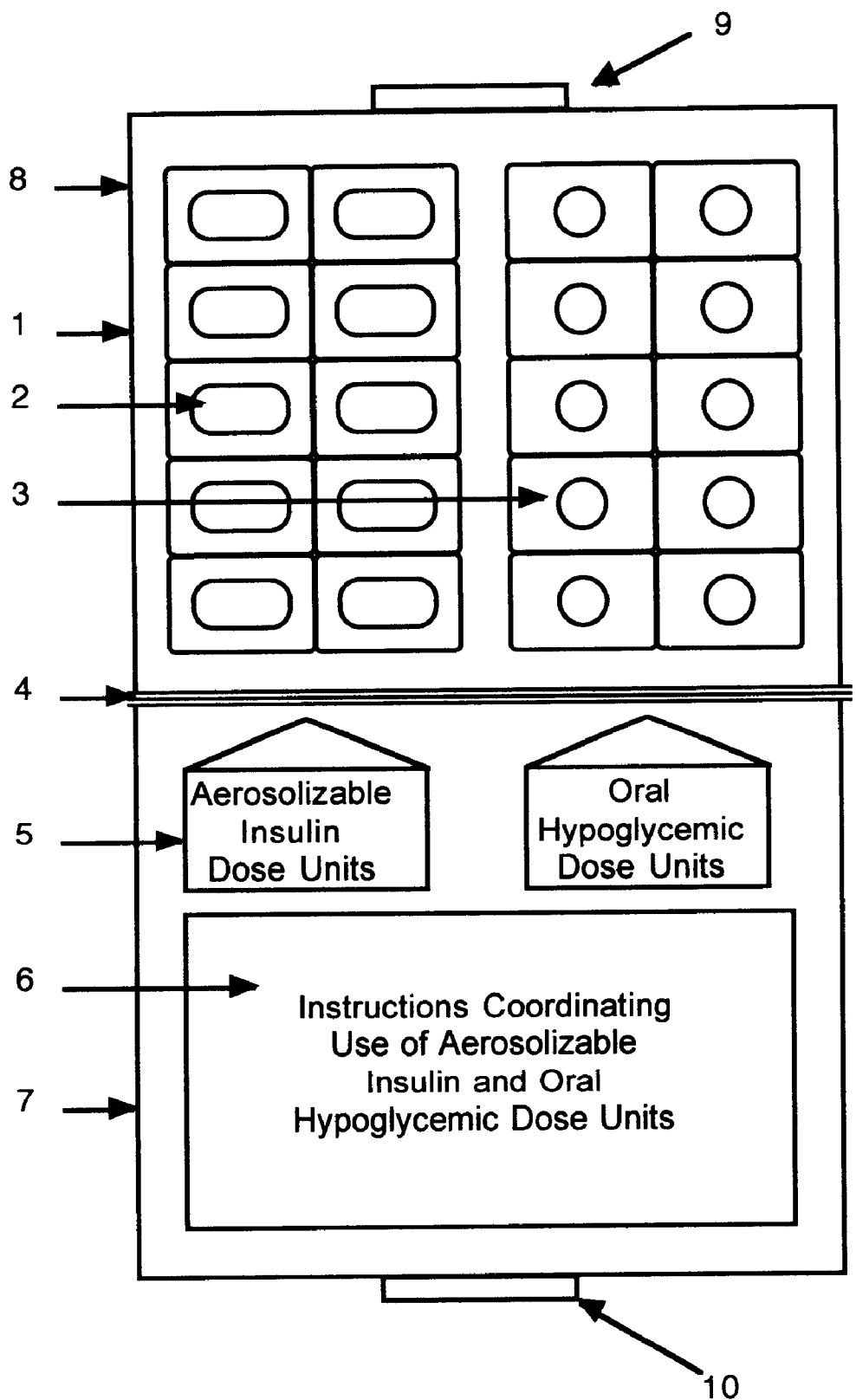
Figure 2:
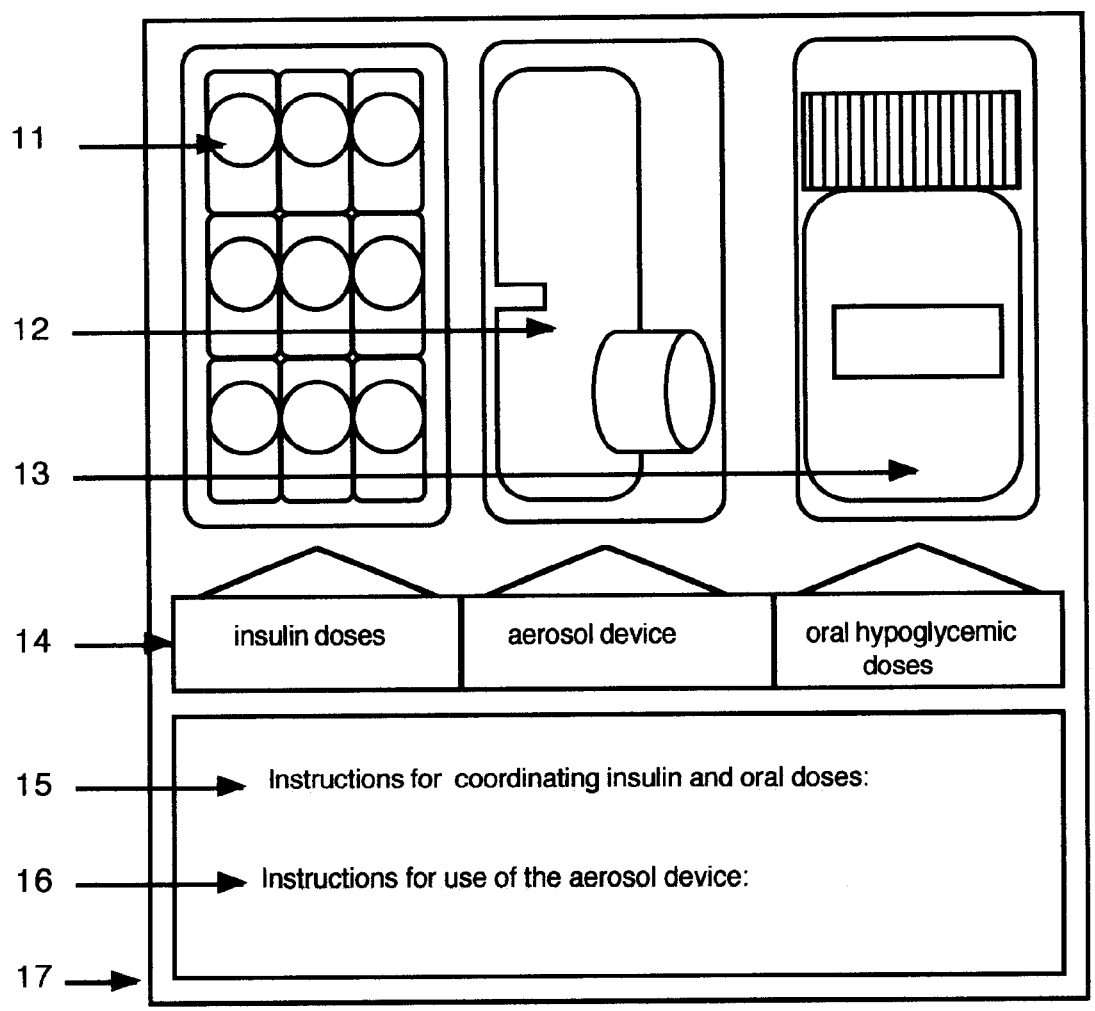

Kuusisto, J. et al., Prandial glucose regulation and cardiovascular disease in Type 2 diabetes, European Journal of Clinical Investigation 1999;29 (Suppl. 2), 7–11.

Heine, R. J., Current therapeutic options in Type 2 diabetes, European Journal of Clinical Investigation 1999;29 (Suppl. 2), 17–20.

Malaisse, W. J., Repaglinide, a new oral antidiabetic agent: a review of recent preclinical studies, European Journal of Clinical Investigation 1999;29 (Suppl. 2), 21–29.

Owens, D. R., Repaglinide: a new short–acting insulinotropic agent for the treatment of Type 2 diabetes, European Journal of Clinical Investigation 1999;29 (Suppl.2), 30–37.

* cited by examiner

METHOD AND DEVICE FOR FACILITATING COMBINED AEROSOL AND ORAL TREATMENTS FOR DIABETES MELLITUS

BACKGROUND OF THE INVENTION

1. Field of the Invention

The present invention relates to a method and device for organizing and coordinating combined aerosol and oral medications for treating diabetes mellitus.

2. Description of the Prior Art

Diabetes mellitus is a chronic illness caused by an effective lack of insulin and manifested by elevation of blood sugar. It is the fourth leading cause of death by disease in the United States and the leading cause of irreversible blindness and chronic renal failure. Treatment for diabetes is directed to lowering blood sugar and to preventing long term complications which include neuropathy, accelerated atherosclerosis, myocardial infarction, gangrene of the lower extremities, retinopathy and nephropathy. Diabetic individuals are typically required to comply with treatments over very long periods to avoid these complications. Measures to enhance convenience and compliance are therefore especially desirable.

The two pharmacological modalities presently used to lower blood sugar are oral hypoglycemic (antidiabetic) agents and insulin. Insulin replacement is presently accomplished by injection and is based upon the lack of insulin or limitation of its action in diabetes mellitus. Oral antidiabetic agents are not chemically akin to insulin and their sugar-lowering mechanism differs from the action of direct insulin replacement. Oral hypoglycemic agents and insulin are, at present, therapeutically utilized alone or in concert with each other, according to the needs of the diabetic individual. Some individuals are best treated with more than one oral agent, with, or without insulin.

Oral hypoglycemic agents presently include sulfonylureas, biguanides, alphaglucosidase inhibitors and thiazolidinediones. Each of these classes operates by a different mechanism, and these agents are known to be used both alone and in various combinations to lower blood sugar. Sulfonureas lower blood sugar by stimulating insulin release from pancreatic islet cells. Examples include tolbutamide, acetohexamide, tolazamide, and chlorpropamide, so-called first-generation agents, and glyburide, glipizide, and glimeperide, second-generation agents. First and second generation sulfonyureas differ in their potency, adverse effects and duration of action. Metformin has an "insulin sparing" action, and is an example of a biguanide. Acarabose has an action of reducing the rate of carbohydrate absorption, and is an example of an alpha-glucosidase inhibitor. Troglitizone acts to potentiate the action of insulin (but has been found to cause idiosyncratic liver injury) and is an example of the thiazolidinedione class.

More recently, an additional agent, the carbamoylmethyl benzoic acid derivative, repaglinide, has become available for treatment in the United States, representing an additional class of oral hypoglycemic agent, the meglitinides. These agents, like the sulfonylureas, stimulate insulin secretion from pancreatic insulin-producing cells, although they are chemically distinct and bind to a different receptor. They can be used alone as well as in concert with other oral agents. Characteristics of the meglitinide analogues, repaglinide and nateglinide, are their rapid absorption, stimulation of insulin release within a few minutes, and rapid biliary excretion, such short action making them particularly useful for the immediate regulation of blood sugar after eating.

Recent clinical studies in diabetic individuals have disclosed that insulin can be administered topically to the nasal and lung mucosa and be absorbed and function to reduce blood sugar. As with injected insulin, oral hypoglycemic medication may be utilized together with insulin administered by respiratory aerosol to lower blood sugar. Because of the more limited action of topical insulin compared to injected insulin, it is likely that topical insulin usage will frequently require complementary use of oral antidiabetic agents for diabetic control.

Compliance with medication therapy is important in successful long-term diabetic care. Health care experts estimate that half of the 1.8 billion prescription medications dispensed yearly are not taken as prescribed. Adherence to medication is known to be adversely affected by inconvenience and complexity of use.

Topical aerosol medications are frequently used to treat respiratory disorders. Poor compliance and frequent errors with aerosol medications are known to occur in treating respiratory disease and results in a relapse of cough, shortness of breath, wheezing, nasal congestion, and chest congestion. The result of non-compliance with diabetes treatment may not result in such apparent consequences, but would rather dispose the individual to long-term, insidious and irreversible damage.

Multiple therapeutic components may be a source of confusion and frustration to users. Individual components lack indicia signifying use of the components together and components may be lost, misplaced, or ignored. Instructions issued separate from medication, as by the physician, may be lost. Furthermore, in spite of careful oral and written instructions from the health care provider, many patients are known to use what they have conveniently available. Haphazard applications of medication can result in treatment failure and in the requirement for additional medical attention and cost.

Cost factors and outcomes are being carefully considered in the current medical climate. Improvements in organization and teaching, including devices and methods to facilitate treatments, are considered desirable in view of limitations in time and costs for medical personnel. Successful therapy is less costly than unsuccessful treatment, which eventuates in complications, multiple clinic visits, or hospitalizations.

Packaging has been developed for aiding the users of medications to comply with proper administration. Dispensing apparatus associated with multiple day administrative drugs are typically directed to the administration of pills or capsules, or similar solid medication.

U.S. Pat. No. 4,039,080, for example, discloses a tray having individual compartments for pills which may contain a week's medication with indicia indicating the day of the week and the time of the day the medication is to be taken.

U.S. Pat. No. 4,553,670 discloses another device comprising a support on which are located two different ingestible medical substances in a single dose form with an adjacent portion for instructional information.

U.S. Pat. No. 4,593,819 discloses a covered pill tray of rectangular configuration having an array of open-topped compartments to hold a supply of medication arranged by the day and time of taking the medication.

U.S. Pat. No. 4,736,849 discloses a method and another type of dispenser for the storage and dispensing of calendar-oriented pills. U.S. Pat. No. 5,181,189 discloses a device for storage and time-regulated dispensing of drugs which includes a drug container to which is secured a signal generator.

U.S. Pat. No. 5,377,841 discloses a sleep therapy package which includes an audio recording for inducing sleep.

U.S. Pat. No. 5,830,490 discloses an organizational tool for a lay person to organize oral medications together with topical medications, and a method for reducing medication error and enhancing therapeutic compliance of combined topical and systemic modality therapeutic regimens. This patent however, does not disclose the application of such devices and methods to the treatment of diabetes.

U.S. Pat. No. 6,187,291 teaches a dispensing container which incorporates an aerosolizable topical insulin preparation, at least one oral hypoglycemic agent, and indicia and instructions for their coordinated use as a single therapeutic regimen for treating diabetes mellitus in a human, in order to make such regimens more convenient, encourage compliance and minimize error. What is not specified is the incorporation of oral agents from the meglitinide class.

Therefore, what is needed is a system that facilitates treatments that utilize topical aerosolized and oral medication together for treating diabetes mellitus in a human. What is further needed is a system that makes such treatment regimens more convenient, encourage compliance and minimize error.

SUMMARY OF THE INVENTION

It is the object of the present invention to provide a system for facilitating treatments that utilize topical aerosolized and oral medication together as a treatment regimen for treating diabetes mellitus in a human. It is a further object of the present invention to provide a system for facilitating treatments that utilize topical aerosolized and oral medication together for treating diabetes mellitus manufactured by a pharmaceutical manufacturer for a user. It is another object of the present invention to provide a system for making such treatment regimens more convenient, encouraging compliance and minimizing error.

The present invention achieves these and other objectives by providing a unifying dispensing container for organizing and instructing diabetes mellitus treatment regimens that combine oral and aerosol medications. The unifying, dispensing container includes oral agents from the meglitinide class, and a method for enhancing the convenience and organization of such combined treatments. The unifying container incorporates a topical insulin preparation and at least one oral hypoglycemic agent, indicia for distinguishing these medications, and instructions for their coordinated use together as a single therapeutic regimen. It is to be understood that multiple doses of insulin and multiple doses of oral hypoglycemic agent are contained therein. The oral hypoglycemic medication may be in the form of tablet, pill, capsule, caplet, packets or containers of liquids, gels, or solids, some of which may require reconstituting, or any generally recognized oral form of medication. The topical insulin preparation may be in powder or liquid form suitable for aerosolization. The dispensing container may contain an aerosolizing device to deliver the insulin, and the insulin may be separate, or incorporated within the aerosolizing device.

BRIEF DESCRIPTION OF THE DRAWINGS

FIG. 1 is a plan view of an embodiment in accordance with the present invention.

FIG. 2 is a plan view of another embodiment in accordance with the present invention.

DETAILED DESCRIPTION OF THE PREFERRED EMBODIMENT

The preferred embodiments of the present invention are illustrated in FIGS. 1–2. Referring to FIG. 1, a support package 1 houses multiple doses of aerosolizable insulin in the form of a dry powder within a blister packaging 2, and multiple doses of oral hypoglycemic agent in the form of tablets in conventional medication tablet-containing blisters 3. A fold 4 in the package is provided in the center. Identifying indicia 5 is provided with respect to the topical insulin and oral hypoglycemic medication. An instruction-bearing portion 6 provides instructions coordinating use of the topical and oral medication of blister packaging 2 and 3, respectively. The instructions are either unalterable or capable of being altered, yet are maintained within the unifying container. The lid portion 7 and the bottom portion 8 of the support package each contain respective clasp portions 9 and 10 which can be secured together when support package 1 is folded along fold 4.

Techniques for preparing and delivering dry powder for pulmonary aerosolization are known, as are adaptations for pulmonary delivery of insulin. Unit doses of powdered insulin may be contained within capsules, blisters, cartridges, or other units. Such containers are typically made of foil and/or plastic, but the use of other materials such as glass or paper is not excluded. Such units are typically opened within the inhaler device, prior to aerosolization and inhalation by the user. Examples include the inhaled insulin delivery devices of Inhale Therapeutic Systems, San Carlos, Calif., the Discus™ Inhaler of Glaxo Wellcome, Inc., of Research Triangle Park, NC., and the Spiros® system, Dura Pharmaceuticals, Inc., of San Diego, Calif..

In the present example, the dry powder insulin blisters 2 are depicted as multiples of nine on a card, each separable from the other, and the dosages are separate from the inhaler device (not shown). Alternatively, a card or cassette containing multiple dosages might be inserted into an inhaler device. As inhaled insulin technology develops, it is anticipated that a variety of means to contain and aerosolize liquid and powder insulin doses will be manufactured.

FIG. 2 depicts another embodiment containing multiple blister doses 11 of aerosolizable insulin, a device 12 for aerosolizing the insulin, multiple doses of oral hypoglycemic medication in a capped bottle 13, and indicia 14 relating to these components. It is to be understood that the multiple doses 11 of insulin might be in liquid or powder form suitable for aerosolization. It is to be further understood that the device for aerosolizing the insulin might be of the Venturi, ultrasonic, or other types presently known for delivery of medical aerosols. The instructions 15 and 16, in this instance, include instructions for transferring insulin blisters 11 to the aerosolization device 12 and for utilizing the aerosolization device 12 to deliver the insulin to the user. Instructions are included for the combined use of the topical and oral medications as a regimen. An example of such a regimen is described below. The unifying container 17 may be closed by conventional means, for example, an attached or detached top (not shown).

Although the embodiments specifically described herein have one aerosolizable medication and one oral medication, packaging containing other numbers of aerosol and oral agent housings are also within the scope of this invention. The packaging may be adapted by widening the packaging and increasing the number of housings and indicia. Additionally, the packaging may be in any geometric configuration, particularly as needed to incorporate aerosol materials and devices as may be desired.

The invention will be further clarified by consideration of the following example, which is intended to be purely exemplary of the invention. A treatment regimen utilizing topical inhaled insulin aerosol and oral hypoglycemic medication for the treatment of diabetes mellitus might be the combined dosing before meals of 2 mg of aerosolized insulin and 1 mg of oral repaglinide. This regimen, given adjacent to mealtime, namely within approximately half an hour before or after meals, would effect blood glucose at the specific time of need. Each agent is presently known to have limited potency and, in some diabetic individuals, to be insufficient to control postprandial hyperglycemia. Both agents are known to have a rapid onset and short duration of action, making them both suitable for short-acting glucose control and for minimizing the potential for hypoglycemia, as may occur with long-acting agents if meals are missed or postponed. This regimen also has advantages of providing exogenous insulin without injections, and of allowing greater flexibility of meal times than might be allowed with long-acting agents. Such a regimen might be further adjusted as, for example, giving one agent before meals and the other after meals. Use of the second agent might be made contingent upon level of monitored blood sugar. Regimens may also be devised to include additional oral agents, and other oral combinations, as well as oral and aerosolized medications of the present invention in combination with conventional injected insulin as fits the need of particular diabetic individuals.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A diabetes mellitus treatment device comprising:
   a dispenser for housing
      multiple dosages of aerosolizable insulin;
      multiple dosages of at least one oral, short-acting hypoglycemic medication which is a carbamoylmethyl benzoic acid derivative;
      indicia operably associated with said dispenser for distinguishing said multiple dosages of said aerosolizable insulin and said multiple dosages of said at least one oral hypoglycemic medication; and
      instructions operably associated with said dispenser for coordinating administration of said multiple dosages of said aerosolizable insulin and said multiple dosages of said at least one oral hypoglycemic medication as a regimen.

2. The device of claim 1 wherein said benzoic acid derivative is one of repaglinide and nateglinide.

3. The device of claim 1 wherein said multiple dosages of said at least one oral hypoglycemic medication is in the form of a tablet, pill capsule, caplet, liquid, powder, or gel.

4. The device of claim 1 wherein said multiple dosages of aerosolizable insulin is in liquid form.

5. The device of claim 1 wherein said multiple dosages of aerosolizable insulin is in powder form.

6. The device of claim 1 further comprising an aerosol device.

7. The device of claim 6 wherein said multiple dosages of said aerosolizable insulin is contained within said aerosol device.

8. A diabetes mellitus treatment device comprising:
   a dispenser for housing
      (a) multiple dosages of aerosolizable insulin;
      (b) multiple dosages of at least one oral hypoglycemic medication selected from the group consisting of sulfonylureas, biguanides, alphaglucosidase inhibitors, thiazolidinediones and meglitinides;
      (c) indicia operably associated with said dispenser for distinguishing said multiple dosages of said aerosolizable insulin and said multiple dosages of said at least one oral hypoglycemic medication; and
      (d) instructions operably associated with said dispenser for coordinating administration said multiple dosages of said aerosolizable insulin and said multiple dosages of said at least one oral hypoglycemic medication as a regimen.

9. The device of claim 8 wherein said multiple dosages of said at least one oral hypoglycemic medication is in the form of a tablet, pill capsule, caplet, liquid, powder, or gel.

10. The divice of claim 8 wherin said multiple dosages of said aerosolizable insulin is in liquid form.

11. The device of claim 8 wherein said multiple dosages of said aerosolizable insulin is in powder form.

12. The device of claim 8 further comprising an aerosol device.

13. The device of claim 12 wherein said multiple dosages of said aerosolizable insulin is contained within said aerosol device.

14. A method of treating diabetes mellitus in a human, said method comprising the steps of:
   (a) providing a dispenser which contains multiple dosage of aerosolizable insulin and multiple dosages of at least one oral hypoglycemic medication selected from the group consisting of sulfonylureas, biguanides, alphaglucosidase inhibitors, thiazolidinediones and meglitinides;
   (b) providing indicia operably associated with said dispenser for distinguishing said multiple dosages of said aerosolizable insulin and said multiple dosages of said at least one oral hypoglycemic medication;
   (c) providing instructions operably associated with said dispenser for teaching the coordinated administration of said multiple dosages of said aerosolizable insulin and said multiple dosages of said at least one oral hypoglycemic medication as a regimen to a user; and
   (d) self-administering said aerosolizable insulin and said at least one hypoglycemic medication.

15. A method of treating diabetes mellitus in a human, said method comprising the steps of:
   (a) providing a dispenser which contains multiple dosage of aerosolizable insulin and multiple dosages of at least one oral short-acting hypoglycemic medication which is a carbamoylmethyl benzoic acid derivative;
   (b) providing indicia operably associated with said dispenser for distinguishing said multiple dosages of aerosolizable insulin and multiple dosages of at least one oral hypoglycemic medication;
   (c) providing instructions operably associated with said dispenser which teach the coordinated administration of aerosolizable insulin and short-acting oral hypoglycemic agent within about a half an hour before or after meals as a regimen, to a user; and
   (d) self-administering said aerosolizable insulin and said at least one oral shortacting hypoglycemic medication.

16. The method of claim 15 wherein said short-acting oral hypoglycemic agent is a meglitinide.

17. A method of treating diabetes mellitus in a human, said method comprising the steps of:
   obtaining a dispenser which contains multiple dosage of aerosolizable insulin, multiple dosages of at least one oral short-acting hypoglycemic medication, indicia for distinguishing said aerosolizable insulin and multiple oral hypoglycemic medication, instructions which teach the coordinated administration of aerosolizable insulin and short-acting oral hypoglycemic agent within about a half an hour before or after meals as a regimen; and taking said aerosolizable insulin and short-acting hypoglycemic agent together as a regimen according to said instructions.

18. The method of claim 17 wherein said short-acting oral hypoglycemic agent is a meglitinide.

* * * * *